US005741817A

United States Patent [19]

Chowhan et al.

[11] Patent Number: 5,741,817
[45] Date of Patent: Apr. 21, 1998

[54] USE OF LOW MOLECULAR WEIGHT AMINO ACIDS IN OPHTHALMIC COMPOSITIONS

[76] Inventors: Masood Chowhan, 2305 Busch Dr., Arlington, Tex. 76014; Bahram Asgharian, 6628 Townlake Cir., Arlington, Tex. 76016; Paul Stach, 2786 Woodstock Rd., Upper Arlington, Ohio 43221

[21] Appl. No.: 575,740

[22] Filed: Dec. 18, 1995

Related U.S. Application Data

[63] Continuation of Ser. No. 279,324, Jul. 22, 1994, abandoned.

[51] Int. Cl.$^6$ ................................................. A61K 31/195
[52] U.S. Cl. ........................................... 514/561; 514/912
[58] Field of Search ................................. 514/561, 912

[56] References Cited

U.S. PATENT DOCUMENTS

| | | | |
|---|---|---|---|
| 4,410,442 | 10/1983 | Lucas et al. | 252/107 |
| 4,504,405 | 3/1985 | Howes | 252/106 |
| 4,525,346 | 6/1985 | Stark | 424/80 |
| 4,710,313 | 12/1987 | Miyajima et al. | 252/105 |
| 5,011,661 | 4/1991 | Schäfer et al. | 422/30 |
| 5,389,369 | 2/1995 | Allen | 424/94.4 |

FOREIGN PATENT DOCUMENTS

| | | | |
|---|---|---|---|
| 560506 | 4/1984 | Australia . | |
| A-18604/88 | 1/1989 | Australia | A01N 63/02 |
| 0 297 598 A2 | 7/1988 | European Pat. Off. . | |
| WO 93/21903 | 11/1993 | WIPO . | |
| WO 95/30414 | 11/1995 | WIPO | A61K 31/20 |

OTHER PUBLICATIONS

Collin, et al., "The Effects of Na$_2$EDTA on Keratocytes and Endothelium of the Isolated Guinea Pig Cornea", *International Contact Lens Clinic*, vol. 9, No. 5, pp. 281–287 (Sep./Oct. 1982).

*Primary Examiner*—Zohreh Fay
*Attorney, Agent, or Firm*—Gregg C. Brown

[57] ABSTRACT

The use of glycine and other low molecular weight amino acids in ophthalmic compositions (e.g., preserved saline solutions) is described. These compounds have been found to enhance the efficacy of antimicrobial preservatives. The compounds also act as chelating agents, buffers and tonicity agents.

7 Claims, No Drawings

USE OF LOW MOLECULAR WEIGHT AMINO ACIDS IN OPHTHALMIC COMPOSITIONS

This is a continuation of application Ser. No. 08/279,324, filed Jul. 22, 1994, abandoned.

BACKGROUND OF THE INVENTION

The present invention relates to the field of ophthalmology. More specifically, the invention relates to the use of glycine and other low molecular weight amino acids in products for treating contact lenses, as well as other ophthalmic products. The amino acids described herein may serve several useful purposes in such compositions, but have been found to be particularly useful in enhancing the activity of antimicrobial preservatives.

Ethylenediaminetetraacetic acid and the monosodium, disodium and trisodium salts thereof (collectively referred to herein as "EDTA") have been widely used for many years in ophthalmic products, particularly products for treating contact lenses. It has been utilized in such products for various purposes, but particularly for its supplemental antimicrobial activity and as a chelating agent. The inclusion of EDTA in contact lens care products and other ophthalmic compositions enhances the antimicrobial efficacy of chemical preservatives contained in such compositions, particularly the efficacy of those preservatives against gram negative bacteria. However, some scientific studies have indicated that EDTA may damage corneal cells. See, e.g., Collin, et al., "The Effects of Na2EDTA on Keratocytes and Endothelium of the Isolated Guinea Pig Cornea", *International Contact Lens Clinic*, volume 9, number 5, September/October 1982. Further, it is incompatible with certain components of compositions for treating contact lenses, such as chlorine, iodine and other oxidizing agents.

In view of the foregoing circumstances, there is a need for a new agent which can perform essentially the same functions as EDTA, but which is more compatible with corneal cells and chemically compatible with oxidizing agents. The new use of glycine and other low molecular weight amino acids described herein is directed to satisfying this need.

SUMMARY OF THE INVENTION

The present invention is based on a new use of glycine and other low molecular weight amino acids. The present inventors have found that such amino acids enhance the activity of antimicrobial preservatives, and are also useful as chelating agents. The low molecular weight amino acids can also serve as buffers and tonicity agents. Based on these properties, glycine and the other amino acids described herein can be utilized in various types of ophthalmic compositions, particularly compositions for treating contact lenses, such as disinfectants, cleaners, comfort drops and rewetting drops, instead of EDTA. The low molecular weight amino acids are particularly useful in preserved saline solutions which are utilized for rinsing and storing contact lenses.

DESCRIPTION OF PREFERRED EMBODIMENTS

The low molecular weight amino acids which may be utilized in the present invention have a molecular weight in the range of from about 75 to about 250. The following compounds are representative of the low molecular weight amino acids which may be utilized in the present invention:

| | |
|---|---|
| L-Alanine | β-Alanine |
| α-Aminoadipic Acid | α-Aminobutyric Acid |
| γ-Aminobutyric Acid | α-Aminoisobutyric Acid |
| Arginine | Asparagine |
| Aspartic Acid | Citrulline |
| Creatine | Glutamic Acid |
| Glycine | Histidine |
| Cystine | Leucine |
| Lysine | Norleucine |
| Ornithine | Phenylalanine |
| Phophoserine | Sarcosine |
| Threonine | Valine |

Amino acids which include alpha (a) carboxylic acid groups are preferred.

The amount of amino acid utilized will depend on the molecular weight of the amino acid(s) selected. In general, one or more of the above-described amino acids will be utilized in a concentration of from about 0.01 to about 7.5 percent by weight/volume ("w/v%").

The preferred amino acid for use in the present invention is glycine. Glycine is a relatively simple, low molecular weight amino acid. It is also known as "aminoacetic acid". The amount of glycine utilized in the compositions of the present invention will vary depending on the type of composition in which it is contained, and the function of glycine in the composition. In general, compositions which contain glycine for purposes of enhancing the antimicrobial activity of the compositions will contain glycine in an amount of from about 0.01 to about 2.5 w/v%., preferably from about 0.1 to about 1.0 w/v%. Similar amounts of glycine will be utilized to perform the other functions mentioned above.

The above-described low molecular weight amino acids may be combined with various ingredients conventionally utilized in ophthalmic products, particularly products for treating contact lenses. More specifically, these compounds may be utilized to enhance the antimicrobial activity of an ophthalmic composition, so as to preserve the composition against microbial contamination. Additionally, such compounds contribute to the tonicity, chelating and buffering properties of the composition.

The low molecular weight amino acids described herein may be included in various types of ophthalmic compositions to enhance antimicrobial activity, or for the other purposes mentioned above. The types of compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or nonaqueous, but will generally be aqueous.

The compositions of the present invention may contain one or more antimicrobial agents to preserve the compositions from microbial contamination. For example, the compositions may contain the antimicrobial agent known as POLYQUAD®; the use of this agent as a preservative in ophthalmic compositions is described in U.S. Pat. No. 4,525,346 (Stark). The entire contents of the Stark 346 patent are hereby incorporated in the present specification by reference. Additional examples of antimicrobial agents include chlorhexidine, alexidine, hexetidine, polyhexamethylene biquanide, benzalkonium chloride, benzododecinum bromide, and other antimicrobial agents utilized as antimicrobial perservatives in ophthalmic compositions. The inclusion of one or more of the above-described low molecular weight amino acids in ophthalmic compositions containing such antimicrobial preservatives enhances the overall antimicrobial activity of the compositions.

As will be appreciated by those skilled in the art, the compositions may also contain a wide variety of other ingredients, such as tonicity agents (e.g., sodium chloride or mannitol), surfactants (e.g., alkyl ethoxylates and polyoxyethylene/polyoxypropylene copolymers), viscosity adjusting agents (e.g., hydroxypropyl methyl cellulose and other cellulose derivatives) and buffering agents (e.g., borates, citrates, phosphates and carbonates). The use of a borate/mannitol buffering system is preferred. The use of such systems is described in copending, commonly assigned U.S. patent application Ser. No. 08/198,427 filed Feb. 21, 1994, and in corresponding PCT International Application Number PCT/US93/04226 (International Publication Number WO 93/21903); the entire contents of the foregoing applications are hereby incorporated in the present specification by reference. The present invention is not limited with respect to the types of ophthalmic compositions in which glycine and the other low molecular weight amino acids described above are utilized. However, the compositions of the present invention preferably do not contain EDTA.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 280–320 milliosmoles per kilogram ("mOsm/kg"). The formulation of compositions for disinfecting and/or cleaning contact lenses will involve similar considerations, as well as considerations relating to the physical effect of the compositions on contact lens materials and the potential for binding or absorption of the components of the composition by the lens.

The following examples are presented to further illustrate the present invention.

EXAMPLE 1

| Ingredient | Concentration (w/v %) |
|---|---|
| Boric Acid | 1.0 |
| Mannitol | 1.5 |
| Glycine | 0.75 |
| Pationic 138C | 0.01 |
| KOH/HCl | pH 7.4 |
| Purified Water | q.s. |

The above composition represents an example of a saline solution which does not contain any conventional antimicrobial preservatives. This composition may be prepared by sequentially adding the ingredients to a portion of the distilled water and stirring the solution until each of the ingredients has dissolved. When all of the ingredients have been dissolved, the solution is brought to final volume by the addition of the remainder of the water, and the pH is adjusted, if necessary. The solution has an osmolality of 295 mOsm/kg. It has been tested and found to meet the United States Pharmacopeia ("USP") and United States Food and Drug Administration ("FDA") requirements for preservative effectiveness; those requirements are referred to below by means of the term "PET", which is an abbreviation for "preservative effectiveness test". The above-described composition is referred to below as "Formulation A".

EXAMPLE 2

The antimicrobial efficacy of Formulation A was evaluated. More specifically, the antimicrobial activity this saline solution was evaluated by inoculating 20 milliliters ("ml") of the solution with 0.1 ml of a microbial suspension. The final concentration was approximately 106 colony forming units per ml. At each time pull, the number of survivors was determined by taking a 1 ml aliquot of the test sample, serially diluting in 9 ml of saline at selected time intervals and preparing pour plates of SCDA. The bacteria and yeast plates were incubated at 30° C. to 35° C. for two to three days. The mold plates were incubated at 20° to 25° C. for five days. The results are presented in Table 1 below.

TABLE 1

Antimicrobial Activity of Formulation A Against PET Microorganisms

| Organism | Time | Log Reduction |
|---|---|---|
| A. niger | 7 Days | 2.5 |
|  | 14 Days | 1.5 |
|  | 21 Days | 1.5 |
|  | 28 Days | 1.4 |
|  | 35 Days | 1.6 |
| C. albicans | 7 days | 3.7 |
|  | 14 Days | 4.7 |
|  | 21 Days | 3.2 |
|  | 28 Days | 4.5 |
| P. aeruginosa | 7 Days | 3.5 |
|  | 14 Days | 5.2 |
|  | 21 Days | 3.1 |
|  | 28 Days | 3.8 |
| E. coli | 7 Days | 3.5 |
|  | 14 Days | 4.9 |
|  | 21 Days | 3.3 |
|  | 28 Days | 3.9 |
| S. aureus | 7 Days | 5.0 |
|  | 14 Days | 5.0 |
|  | 21 Days | 4.9 |
|  | 28 Days | 4.6 |

EXAMPLE 3

| Ingredient | Concentration (w/v %) |
|---|---|
| Boric Acid | 0.442 |
| Sodium Borate | 0.0875 |
| Glycine | 1.61 |
| Pationic 138C | 0.01 |
| Purified Water | q.s. |

The above composition, which is referred to herein as "Formulation B", represents an example of a saline solution containing a relatively high concentration of glycine in a borate buffer. This solution was prepared by means of a procedure similar to the procedure described in Example 1 above. The pH of the solution was 7.6 and the osmolality was 295 mOsm/kg. The antimicrobial activity of Formulation B was evaluated against a gram negative and a gram positive bacteria by means of the procedures described in Example 2. The solution showed a 2.2 log reduction against S. aureus and a 3.8 log reduction against P. aeruginosa at 7 days.

EXAMPLE 4

The following compositions were tested to determine if EDTA could simply be eliminated from saline solutions; the compositions were prepared by means of procedures similar to the procedure described in Example 1 above:

| Ingredient | Concentration (w/v %) | | |
|---|---|---|---|
| | Formulation C | Formulation D | Formulation E |
| Boric Acid | 0.442 | 0.442 | 0.442 |
| Sodium Borate | 0.0875 | 0.0875 | 0.0874 |
| Sodium Chloride | 0.675 | 0.675 | 0.675 |
| Pationic 138C | — | 0.01 | 0.01 |
| Disodium Edetate | — | — | 0.1 |
| Purified Water | q.s | q.s. | q.s. |

Formulation C has a pH of 7.7 and osmolality of 299 mOsm/kg, Formulation D has a pH of 7.7 and osmolality of 294 mOsm/kg, and Formulation E has a pH of 7.3 and osmolality of 305 mOsm/kg. The compositions were tested for antimicrobial activity by means of the procedures described in Example 2. The results, expressed as the number of log reductions after 7 days, are listed below:

| Antimicrobial Activity (i.e., Log Reduction at Day 7) Against PET Microorganisms | | | |
|---|---|---|---|
| | Formulation C | Formulation D | Formulation E |
| A. niger | 1.8 | 1.9 | 1.0 |
| P. aeruginosa | 0.0 | 0.4 | 4.1 |
| S. aureus | 1.6 | 4.1 | 5.0 |

Both Formulation C and Formulation D failed USP and FDA requirements for preservative effectiveness, while Formulation E met those requirements. These results clearly demonstrate that EDTA cannot simply eliminated. This is particularly true relative to *Pseudomonas aeruginosa*. However, the results presented in Examples 2 and 3 demonstrate that EDTA can be replaced by low molecular weight amino acids, such as glycine.

EXAMPLE 5

| Ingredient | Concentration (w/v %) |
|---|---|
| Boric acid | 0.35 |
| Sodium borate | 0.11 |
| Mannitol | 1.5 |
| Glycine | 0.75 |
| Polyquad | 0.001 |
| Purified water | q.s. |

The above composition represents an example of the preserved saline solutions of the present invention, wherein a low molecular weight amino acid is utilized to augment the activity of a conventional antimicrobial preservative. This composition may be prepared by sequentially adding the listed ingredients to 90 ml of purified water and stirring until each ingredient has dissolved. The pH is adjusted to 7.4 and the volume is adjusted to 100 ml. The low molecular weight amino (i.e., glycine) contributes to the antimicrobial properties of the solution, as well as to the tonicity and chelating properties of the solution.

EXAMPLE 6

| Ingredient | Concentration (w/v %) |
|---|---|
| Polyvinyl alcohol | 0.75 |
| Hydroxyethyl cellulose | 0.28 |
| Boric acid | 0.35 |
| Sodium borate | 0.11 |
| Mannitol | 2.0 |
| Glycine | 0.5 |
| Polyquad ™ | 0.001 |
| Purified water | q.s. |

The above composition is an example of a composition for lubricating contact lenses or increasing the comfort of contact lenses when worn by patients. The composition is prepared in two parts and then recombined. In order to prepare the first part, polyvinyl alcohol and hydroxyethyl cellulose are dispersed in 40 ml of purified water at a temperature of 50°–70° C., and then allowed to hydrate and cool to room temperature. The solution is then Polish filtered using a 5–20 micrometer ("pm") membrane filter and autoclaved. In order to prepare the second part, the remaining ingredients are dissolved in 50 ml of purified water. This solution is then sterile filtered using a 0.22 μm membrane filter into a sterile receiving container. The first part and the second part are then combined aseptically and the pH of the resulting solution is adjusted to 7.4. The volume of the solution is then brought to 100 ml with purified water. The solution has an osmolality of 230–260 mOsm/kg.

The use of a low molecular weight amino acid in this composition enhances the antimicrobial activity of the composition, and also eliminates the need for an additional tonicity agent, such as sodium chloride.

EXAMPLE 7

| Ingredient | Concentration (w/v %) |
|---|---|
| Polaxamine | 0.25 |
| Boric acid | 0.5 |
| Mannitol | 1.5 |
| Sodium chloride | 0.15 |
| Glycine | 0.25 |
| Polyhexamethylene biquanide | 0.0005 |
| Purified water | q.s. |

The above composition is an example of a multi-purpose solution for cleaning, disinfecting and storing contact lenses. The composition was prepared by sequentially adding the ingredients to 90 ml of purified water and stirring until each ingredient was dissolved. The pH of the resulting solution was adjusted to 7.4, and the volume was adjusted to 100 ml with purified water. The low molecular weight amino acid performs the same function in this composition as in the other compositions described above.

What is claimed is:

1. A method of enhancing the antimicrobial activity of an ophthalmic composition which comprises adding to the composition an effective amount of a low molecular weight amino acid, said amino acid including an alpha carboxylic acid group and having a molecular weight of 75 to 250, wherein the ophthalmic composition does not contain EDTA.

2. A method according to claim 1, wherein the amino acid comprises glycine.

3. A method according to claim 1, wherein the composition is a contact lens disinfecting solution.

4. A method according to claim 2, wherein the composition is a contact lens disinfecting solution.

5. A method according to claim 1, wherein the composition is a saline solution adapted for rinsing and storing contact lenses.

6. A method according to claim 5, wherein the low molecular weight amino acid comprises glycine in an amount effect to preserve the saline solution from microbial contamination.

7. A method according to claim 6, wherein the saline solution has the following formula:

| Ingredient | Concentration (w/v %) |
|---|---|
| Boric Acid | 1.0 |
| Mannitol | 1.5 |
| Glycine | 0.75 |
| Pationic 138C | 0.01 |
| KOH/HCl | pH 7.4 |
| Purified Water | q.s.. |

* * * * *